United States Patent [19]

Yang

[11] Patent Number: 4,483,941
[45] Date of Patent: Nov. 20, 1984

[54] CATALYSTS FOR ALKOXYLATION REACTIONS

[75] Inventor: Kang Yang, Ponca City, Okla.

[73] Assignee: Conoco Inc., Ponca City, Okla.

[21] Appl. No.: 414,216

[22] Filed: Sep. 2, 1982

[51] Int. Cl.$^3$ .................. B01J 31/02; B01J 31/12; B01J 31/14
[52] U.S. Cl. .................. 502/171; 502/152; 502/203; 502/227; 502/231; 568/618; 544/185
[58] Field of Search .................. 502/171

[56] References Cited

U.S. PATENT DOCUMENTS

| | | | |
|---|---|---|---|
| 3,244,646 | 4/1966 | Naro et al. | 502/171 X |
| 3,402,164 | 9/1968 | Miyoshi et al. | 502/171 X |
| 3,773,733 | 11/1973 | Matsushima | 502/171 X |
| 3,860,622 | 1/1975 | Wade | 502/171 X |

*Primary Examiner*—Patrick Garvin
*Attorney, Agent, or Firm*—Cortlan R. Schupbach

[57] ABSTRACT

Catalysts producing a sharply peaked alkoxylation distribution during the alkoxylation of organic materials comprise mixtures of $BF_3$ and metal alkyls or metal alkoxides, $SiF_4$ and metal alkyls or metal alkoxides, or mixtures of these catalysts.

2 Claims, No Drawings

CATALYSTS FOR ALKOXYLATION REACTIONS

This invention relates to the production of alkoxylated organic compounds by reacting said compounds with an alkoxylating agent in the presence of $BF_3$ or $SiF_4$ together with metal alkyls or metal alkoxides. More particularly, this invention relates to the production of alkoxylated organic compounds by reacting said compounds with the catalysts of the present invention in the presence of alkoxylating agents to yield a very sharply peaked alkoxylate distribution in the product.

In general, the reaction of a variety of organic materials together with an adducting material such as ethylene oxide or propylene oxide to form alkoxylated materials is well known in the art. U.S. Pat. No. 2,683,087 discloses that water adsorption by paper articles is improved by the use of amine adducts of ethylene oxide. British Pat. No. 847,714 teaches the processing of prehydrolyzed sulfate wood pulp into viscose by incorporating a propylene oxide/ethylene oxide adduct of ethylene diamine. French Pat. No. 1,122,729 discloses the use of acylarylpolyglycol adduct to the viscose pulp or slurry. Belgium Pat. No. 555,529 discloses an antistatic agent for synthetic fibers produced by esterifying one mole of lauric acid with one mole of an ethoxylated glycerol British Pat. No. 763,215 suggests an ethoxylated organic sulfamide as an anti-static agent for textiles.

British Pat. No. 705,117 discloses an emulsifier combination for pesticides comprising a mixture including a tall oil or dodecyl mercaptan adduct. Polyhydric alcohol ethoxylates find uses in foods and feeds as shown by U.S. Pat. No. 2,674,534 which discloses the use of sorbitol laurate and sorbitol oleate adducts in the coating of ice cream bars. Alkylene oxide adducts are also used in the leather industry in formulations for tanning, dyeing, and lubricating leather. Adducts of organic materials also have a variety of uses and metal working industries where ester, ether and amine adducts are the products used most frequently. Ethylene oxide adducts such as sorbitan monostearate adducts have been found useful in pharmaceutical and cosmetic preparations and are used to provide activities such as drug carriers, emulsifiers and solubilizers. Ethylene oxide adducts of nonyl phenols have been used to produce detertents and cleaning agents, domestic and industrial laundry detergents, detergent builders, polishers, sanitizers, and dry cleaning materials. Alkyl phenol adducts are especially good soil suspending materials when used in detergent formulations since they possess excellent detergency, fat emulsifying power, concentration effect, chemical resistance, hard water stability and pH properties.

Much literature is available in the general area of alcohol alkoxylation. These references relate to the catalytic ability of various materials in the mechanism of kinetics of these reactions. For example, French Pat. No. 1,365,945 teaches the use of compounds containing an active hydrogen atom reacted with ethylene oxide in the presence of an alkali metal base.

Both basic and acidic catalysts in general are known to produce alkoxylation of organic materials. However, alkoxylation of these materials invariably produces a distribution of various adducts. For example, in surfactant applications, an adduct of too few ethylene oxide molecules is not effective because of poor solubility. In contrast, an adduct with too many ethylene oxide molecules is likewise undesirable because surface tension reduction per unit mass decreases drastically as the molecular weight increases. Thus it has long been essential to produce and use alkoxylates with as sharp a distribution in the desired mole adduct range for the particular use of the material as can possibly be realized.

Normally, acid catalyzed reactions produce such alkoxylates, but these catalysts produce harmful side products which must be separated and removed prior to use. Base catalysts normally do not produce the level of by-products which acidic catalysts do, but provide a much broader distribution of alkoxylation adducts, thus making them economically unsuitable. Thus both methods have disadvantages.

Therefore, it would be desirable to provide a catalyst system for the alkoxylation of organic materials which provides low by-product levels, typical of base catalysts, yet provides a narrow distribution of the preferred mole adducts, normally obtained from acid catalysts. Such a catalyst would promote the narrowing of product distribution curve and would contribute significantly to the intrinsic value of the alkoxylate produced.

Such a catalyst is described in U.S. Pat. Nos. 4,239,917 and 4,306,093. However, these catalysts, while effective in producing a very sharply peaked distribution product, do not produce alkoxylate peaks as sharp as the catalysts to be described herein.

The use of dialkyl aluminum fluoride or alkyl aluminum difluoride is known as a catalyst for the polymerization of epoxides to produce polyalkoxy alcohols as described in U.S. Pat. Nos. 3,029,217 and 3,313,743. However, these catalysts were not used in the alkoxylation of alcohols and require water in the polymerization described. In addition, dialkyl aluminum halides or alkyl aluminum dihalides can be used to produce ethoxylated alcohols using different methods, such as the polymerization of ethylene oxide described in U.S. Pat. No. 3,321,533. However, in this process the materials are not used as catalysts, but rather as reactants since sodium hydroxide acts as the ethoxylation catalyst.

U.S. Pat. No. 3,395,185 utilizes organoaluminum zinc compounds as catalysts in the preparation of low molecular weight polyoxymethylene glycols. Zinc, however, is not an effective catalyst in the present invention. U.S. Pat. No. 2,716,137 uses nitrogen containing catalysts. These materials are characterized by low reaction rates and objectionable odors. U.S. Pat. No. 4,282,387 uses catalysts such as calcium, strontium and barium acetates and naphthenates. These materials produce alkoxylate products more sharply peaked than current commercial basic catalysts such as sodium and potassium hydroxide, but do not provide the extremely high peaking of the present invention.

The ethoxylation of alcohols using aluminum compounds such as aluminum trifluoride or trialkyl aluminum is described in U.S. Pat. Nos. 2,879,220; 3,350,462; 3,719,636 and 3,969,417. Preparation of alkoxylated alcohols using a latent catalyst comprising a mixture of $BF_3$ and trialkyl phospheric is shown in U.S. Pat. No. 3,597,502 and 3,910,878. Zinc dialkyl catalysts for alcohol alkoxylation are shown in U.S. Pat. No. 3,395,185.

It is therefore an object of the present invention to provide a catalyst system which will yield a narrow alkylene oxide adduct distribution in the alkoxylation of organic materials, while providing low levels of undesirable by-products and non-desired alkoxylation adducts. Other objects will become apparent to those skilled in this art as the description proceeds.

It has now been discovered according to the instant invention that alkoxylation of organic materials can be carried out in the presence of at least one catalyst comprising $BF_3$ and metal alkyls, $SiF_4$ and metal alkyls or mixtures of these catalysts, wherein the metal alkyls have the general formula $M(R)_n$ wherein each R is, independently, hydrogen and alkyl groups containing from 1 to 20 carbon atoms, and wherein M is selected from the group consisting of aluminum, galluim, indium, thallium, titanium, zirconium and hafnium, and n is 3 or 4, depending on valence of M. Aluminum and titanium metal alkyls are preferred. These alkyl groups will normally contain from about 1 to about 20 carbon atoms each, but the preferred catalysts are those containing from about 1 to about 14 carbon atoms each.

Representative but non-exhaustive examples of such catalysts are $BF_3$/aluminum hydride, $BF_3$/trimethylaluminum, $BF_3$/triethylaluminum, $BF_3$/tripropylaluminum, $SiF_4$/aluminum hydride, $SiF_4$/trimethylaluminum, $SiF_4$/triethylaluminum, $BF_3$/dimethyl ethyl aluminum, $SiF_4$/dimethyl ethyl aluminum, $BF_3/(C_{20}H_{41})_3Al$, $SiF_4/(C_{20}H_{41})_3Al$, $BF_3$/titanium hydride, $BF_3$/tetramethyltitanium, $BF_3$/tetraethyltitanium, $BF_3$/tetrapropyltitanium, $SiF_4$/titanium hydride, $SiF_4$/tetramethyltitanium, $SiF_4$/tetraethyltitanium, $BF_3$/dimethyl diethyl titanium, $SiF_4$/dimethyl diethyl titanium, $BF_3/(C_{20}H_{41})_4Ti$, $SiF_4/(C_{20}H_{41})_4Ti$, $BF_3$/trimethyl gallium; $BF_3$/trimethyl indium; $BF_3$/trimethyl thallium, $BF_3$/tetramethyl zirconium, $SiF_4$/tetramethyl hafnium.

Catalysts which provide similar adduct distributions but which are less expensive comprise $BF_3$ and metal alkoxides, $SiF_4$ and metal alkoxides, or mixtures of these catalysts, wherein the metal alkoxides have the general formula $M(OR)_n$ where each R is, independently, hydrogen and alkyl groups containing from 1 to 20 carbon atoms each, M is aluminum or titanium, and n is 3 or 4 depending on valence of M. Preferred catalyst are those containing from 1 to 14 carbon atoms in each alkyl group.

Representative but non-exhaustive examples of such catalysts are $BF_3/(C_2H_5O)_3Al$; $BF_3/(CH_3O)_3Al$; $SiF_4/(C_2H_5O)_3Al$; $SiF_4/(CH_3O)_3Al$; $BF_3/(CH_3O)_2(C_2H_5O)Al$; $SiF_4/(CH_3O)_2(C_2H_5O)Al$; $SiF_4/(CH_3O)(C_2H_5O)_2Al$; $BF_3/(CH_3O)_3Al$; $BF_3/(C_2H_5O)_3Al$; $BF_3/(C_{20}H_{41}O)_3Al$; $BF_3/C_2H_5O)_4Ti$; $BF_3/(CH_3O)_4Ti$; $SiF_4/(C_2H_5O)_4Ti$; $SiF_4/(CH_3O)_4Ti$; $BF_3/(CH_3O)_2(C_2H_5O)_2Ti$; $BF_3/(CH_3O)_2(C_2H_5O)_2Ti$ and $SiF_4/(CH_3O)_2(C_2H_5O)_2Ti$.

The instant invention can be carried out at temperatures of from about 20° C. to about 260° C. However, more normal temperatures range from about 90° C. to about 200° C. For practical purposes, most commercial operations will be carried out in the temperature range of from about 100° C. to about 200° C.

$BF_3$ is a known alkoxylation catalyst at lower temperatures, 100° C. or lower. However, $BF_3$ is normally added to the reaction in a gaseous form. When present in this form, and at these temperatures, the presence of water in the reaction forms high levels of by-products which are undesirable and difficult to separate, such as polyethylene glycol and dioxane.

The catalysts of the present invention can be used in the processes described when carried out at ambient pressure. However, pressures above or below ambient can be used as desired. Pressure or lack of pressure is not a critical factor in the present invention and pressures may be used as convenient. Normally pressures of up to about 100 pounds per square inch (psig) can be used, but pressures below about 60 psig are preferred. It is simply more convenient to normally carry out the reactions in the pressure range of from about atmospheric to about 100 psig.

The alkoxylations of the present invention are normally carried out with materials or mixtures of materials comprising alpha and beta alkylene oxide. Of these materials, ethylene oxide, propylene oxide or mixtures of these are preferred. However, the process and catalysts of the present invention will be effective for any adducting material desired.

The reaction products can have any desired content of adducting material. For example, in alcohol alkoxylations, ethylene oxide will normally comprise from about 30 to about 90% of product content based on weight. However, for most purposes the content of ethylene oxide will range from about 40% to about 70% by weight. The weight of adducting material present in the reaction is not critical other than the minimum amount necessary to provide sufficient units to reach the mole adduct level desired for the materials to be reacted.

For practical purposes, normally from about 0.05 to about 5.0 weight percent catalyst based upon the weight of the material to be reacted is present in the reaction. Preferred levels of catalysts in the reaction mixture are from about 0.1 to about 3.0% by weight based on the total reaction mixture weight.

The catalysts of the present invention are normally added to the reaction mixture in a solution form. However, in order to render these catalysts less air sensitive and more stable, catalysts can optionally be supported on materials having active surface hydroxyl groups. Representative but non-exhaustive examples of such supports are alumina, diatomaceous earth, silica, bentonite glass, various clays and the like.

When utilizing the catalysts of the present invention, normally the catalysts are used in mole ratios of $BF_3$ to $SiF_4$ to metal alkyls or metal alkoxides of from about 0.1 to about 10 but from about 0.2 to about 2 are preferred.

If desired, the catalysts of the present invention can be prepared separately and added to the reactor either together or separately, or can be prepared separately, placed in an inert solvent for handling ease and placed in the reactor, or can be combined with the metal alkyls or alkoxides prior to insertion into the reactor, either alone or in the presence of an inert solvent. The relationship between $BF_3$ and/or $SiF_4$ and the normally inert metal alkyls and metal alkoxides is not clear, but apparently the mere presence of metal alkyls and metal alkoxides provides the sharpened distribution of the present invention.

Representative examples of inert solvents useful in the present invention include the saturated aliphatic hydrocarbons and low polynuclear aromatic hydrocarbons. Such inert solvents include heptane, hexane, octane, nonane, and decane.

The catalysts described herein do not impart large shifts in pH to a reaction system as do NaOH or $BF_3$ alone. In the catalyzed system of the present invention, pH has little meaning.

The catalysts of the present invention are useful for the alkoxylation of organic materials which can normally be alkoxylated. Among such materials are alcohols, whether polyhydric, unsaturated, linear or branched; saturated alcohols, alkyl phenols, polyols, aldehydes, ketones, amines, amides, organic acids and mercaptans.

These organic materials are normally selected from the group consisting of (a) polyhydric alcohols containing a total of 2 to 30 carbon atoms and having the general formula

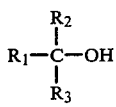

wherein $R_1$, $R_2$, and $R_3$ are, independently, linear or branched acyclic groups, alicyclic groups, aryl groups, cyclic groups, or hydrogen and wherein the R-designated groups can in addition contain one or more functional groups selected from the group consisting of amine, carboxyl, hydroxy, halogen, nitro, carbonyl, and amide;

(b) aldehydes and ketones having boiling points above 100° C. and containing a total of from 2 to 30 carbon atoms, and having one or more carbonyl containing compounds of the general formula

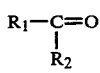

wherein $R_1$ and $R_2$ are, independently, hydrogen, linear or branched acyclic groups, alicyclic groups, cyclic groups, or aryl groups and wherein the R-designated groups can in addition contain one or more functionalities selected from the group consisting of carboxyl, hydroxyl, halogen, nitro, amine, or amide;

(c) primary, secondary or tertiary amides having a boiling point of above 100° C. and containing a total of from 1 to 30 carbon atoms and containing 1 or more amide containing compounds of the general formula

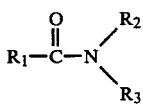

wherein $R_1$, $R_2$, and $R_3$ are, independently hydrogen, linear or branched acyclic groups, alicyclic groups, cyclic groups, or aryl groups and wherein the R-designated groups can in addition contain one or more other functionalities selected from the group consisting of hydroxyl, carboxyl, carbonyl, amine, nitro, or halogen;

(d) primary, secondary or tertiary amines having a boiling point above 100° C., containing from a total of 1 to 30 carbon atoms and containing 1 or more amine containing compounds of the general formula

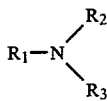

wherein $R_1$, $R_2$, and $R_3$ are, independently, hydrogen, linear or branched acyclic groups, alicyclic groups, cyclic groups, or aryl groups, and wherein the R-designated groups can in addition contain one or more functionalities selected from the group consisting of hydroxyl, carbonyl, halogen, carboxyl, nitro or amide;

(e) organic acids having a boiling point of above 100° C., containing from a total of 1 to 30 carbon atoms and having 1 or more carboxylic acid containing compounds of the general formula

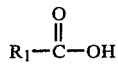

wherein $R_1$ is a hydrogen, a linear or branched acyclic group, alicyclic group, cyclic group, or aryl group and wherein the R group can in addition contain one or more functionalities selected from the group consisting of carbonyl, hydroxyl, halogen, nitro, amine, or amide;

(f) alkyl phenols having a boiling point of above 100° C., containing a total of from 6 to 30 carbon atoms and having 1 or more compounds of the general formula

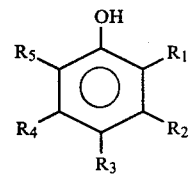

wherein $R_1$, $R_2$, $R_3$, $R_4$, and $R_5$ are, independently, hydrogen, halogen, hydroxyl, nitro, or carbonyl, linear or branched acyclic groups, alicyclic groups cyclic groups, aryl groups, or substituted aryl groups and wherein in addition the R-designaged groups can contain one or more functionalities selected from the group consisting of halogen, ether, nitro, carboxyl, carbonyl amine, amide, or hydroxyl;

(g) mercaptans of the general formula

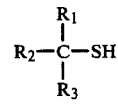

wherein $R_1$, $R_2$ and $R_3$ are, independently, hydrogen, linear or branched acyclic groups, alicyclic groups, cyclic groups or aryl groups containing from 1 to 30 carbon atoms and wherein the $R_1$, $R_2$ or $R_3$ designated groups can in addition contain one or more functionalities selected from the group consisting of carboxyl, hydroxyl, halogen, nitro amine, or amide, and (h) alcohols of the general formula ROH where R is a linear or branched alkyl group containing from 1 to 30 carbon atoms, an aryl group or a cyclic group containing from 6 to 30 carbon atoms, or an olefinic or acetylenic group containing from 1 to 30 carbon atoms.

While the instant invention is effective with all classes of alcohols, both saturated and unsaturated, saturated alcohols are preferred. Of these, alkanols are most preferred. The primary, secondary linear and branched, linear and branched primary alkanols are the most commonly used and are the preferred materials for alkoxylation using the present invention.

Representative but non-exhaustive examples of alcohols which can be alkoxylated according to the present invention are 1-dodecanol; 1-tridecanol; 1-tetradecanol; 1-pentadecanol; 1-hexadecanol; 1-heptadecanol; 1-octadecanol; 1-nonadecanol; 1-eicosanol; 1-docosanol; 2-methyl-1-undecanol; 2-propyl-1-nonanol; 2-butyl-1-octanol; 2-methyl-1-tridecanol; 2-ethyl-1-dodecanol; 2-propyl-1-undecanol; 2-butyl-1-decanol; 2-pentyl-1-nonanol; 2-hexyl-1-octanol; 2-methyl-1-pentadecanol; 2-ethyl-1-tetradecanol; 2-propyl-1-tridecanol; 2-butyl-1- dodecanol; 2-pentyl-1-undecanol; 2-hexyl-1-decanol; 2-heptyl-1-decanol; 2-hexyl-1-nonanol; 2-octyl-1-octanol; 2-methyl-1-heptadecanol; 2-ethyl-1-hexadecanol; 2-propyl-1-pentadecanol; 2-butyl-1-tetradecanol; 1-pentyl-1-tridecanol; 2-hexyl-1-dodecanol; 2-octyl-1-decanol; 2-nonyl-1-nonanol; 2-dodecanol; 3-dodecanol; 4-dodecanol; 5-dodecanol; 6-dodecanol; 2-tetradecanol; 3-tetradecanol; 4-tetradecanol; 5-tetradecanol; 6-tetradecanol; 7-tetradecanol; 2-hexadecanol; 3-hexadecanol; 4-hexadecanol; 5-hexadecanol; 6-hexadecanol; 7-hexadecanol; 8-hexadecanol; 2-octadecanol; 3-octadecanol; 4-octadecanol; 5-octadecanol; 6-octadecanol; 7-octadecanol; 8-octadecanol; 9-octadecanol; 9-octadecenol-1; 2,4,6-trimethyl-1-heptanol; 2,4,6,8-tetramethyl-1-nonanol; 3,5,5-trimethyl-1-hexanol; 3,5,5,7,7-pentamethyl-1-octanol; 3-butyl-1-nonanol; 3-butyl-1-undecanol; 3-hexyl-1-undecanol; 3-hexyl-1-tridecanol; 3-octyl-1-tridecanol; 2-methyl-2-undecanol; 3-methyl-3-undecanol; 4-methyl-4-undecanol; 2-methyl-2-tridecanol; 3-methyl-3-tridecanol; 4-methyl-3-tridecanol; 4-methyl-4-tridecanol; 3-ethyl-3-decanol; 3-ethyl-3-dodecanol; 2,4,6,8-tetramethyl-2-nonanol; 2-methyl-3-undecanol; 2-methyl-4-undecanol; 4-methyl-2-undecanol; 5-methyl-2-undecanol; 4-ethyl-2-decanol; 4-ethyl-3-decanol; tetracosanol; hexacosanol; octacosanol; triacontanol; dotriacontanol; hexatriacontanol; 2-decyltetradecanol; 2-dodecylhexadecanol; 2-tetradecyloctadecanol; 2-hexadecyleicosanol, and unsaturated alcohols such as 1-hexyn-3-ol; oleyl alcohol (technically names cis-9-octadecene 1-ol); 2,5-dimethyl-4-octyne-3,6-diol; 2,4,7,9-tetramethyl-n-decyne-4,7-diol; 3-dodecene-1-ol; and 3,6-dimethyl-8-dodecene-1-ol.

Representative but non-exhaustive examples of various polyhydric alcohols which can be alkoxylated according to the present invention are
ethylene glycol
1,2-propylene glycol
1,4-butanediol
1,6-hexanediol
1,10-decanediol
1,3-butylene glycol
diethylene glycol
diethylene glycol monobutyl ether
diethylene glycol monomethyl ether
diethyl glycol monoethyl ether
dipropylene glycol
dipropylene glycol monomethyl ether
ethylene glycol monomethyl ether
ethylene glycol monoethyl ether
ethylene glycol monobutyl ether
hexylene glycol
mannitol
sorbitol
pentaerythritol
dipentaerythritol
tripentaerythritol
trimethylolpropane
trimethylolethane
neopentyl glycol
diethaholamine
triethanolamine
diisopropanolamine
triisopropanolamine
1,4-dimethylolcyclohexane
2,2-bis(hydroxymethyl)propionic acid
1,2-bis(hydroxymethyl)benzene
4,5-bis(hydroxymethyl)furfural
4,8-bis(hydroxymethyl)tricyclo[5,2,1,0]decane
tartaric acid
2-ethyl-1,3-hexanediol
2-amino-2-ethyl-1,3-propanediol
triethylene glycol
tetraethylene glycol
glycerol
ascorbic acid Representative but non-exhaustive examples of various aldehydes and ketones which can be alkoxylated according to the present invention are
lauryl aldehyde
benzaldehyde
2-undecanone
acetophenone
2,4-pentandione
acetylsalicyclic acid
ortho-chlorobenzaldehyde
para-chlorobenzaldehyde
cinnamic aldehyde
diisobutyl ketone
ethylacetoacetate
ethyl amyl ketone
camphor
para-hydroxybenzaldehyde
2-carboxybenzaldehyde
4-carboxybenzaldehyde
salicylaldehyde
octyl aldehyde
decyl aldehyde
p-methoxybenzaldehyde
p-aminobenzaldehyde
phenylacetaldehyde
acetoacetic acid
2,5-dimethoxybenzaldehyde
1-naphthyl aldehyde
terephthaldehyde Representative but non-exhaustive examples of amides which can be alkoxylated according to the instant invention are:
formamide
benzamide
acetanilide
salicylamide
acetoacetanilide
ortho-acetoacetotoluidide
acrylamide
N,N-diethyltoluamide
N,N-dimethylacetamide
N,N-dimethylformamide
phthalimide
octylamide
decylamide
laurylamide
stearylamide
N,N-dimethyllaurylamide
N,N-dimethylacrylamide
para-chlorobenzamide
para-methoxybenzamide
para-aminobenzamide
para-hydroxybenzamide
ortho-nitrobenzamide
N-acetyl-para-aminophenol
2-chloroacetamide
oxamide
N,N-methylene-bis-acrylamide Representative but non-exhaustive examples of amines which can be alkoxylated according to the present invention are:
aniline
benzylamine
hexadecylamine
triphenylamine
aminoacetic acid
anthranilic acid
cyclohexylamine
tert-octylamine
ortho-phenylenediamine
meta-phenylenediamine
para-phenylenediamine
N-acetyl-para-aminophenol
2-amino-4-chlorophenol
2-amino-2-ethyl-1,3-propanediol
ortho-aminophenol
para-aminophenol
para-aminosalicylic acid
benzyl-N,N-dimethylamine
tert-butylamine
2-chloro-4-aminotoluene
6-chloro-2-aminotoluene
meta-chloroaniline
ortho-chloroaniline
para-chloroaniline
4-chloro-2-nitroaniline
cyclohexylamine
dibutylamine
2,5-dichloroaniline
3,4-dichloroaniline
dicyclohexylamine
diethanolamine
N,N-diethylethanolamine
N,N-diethyl-meta-toluidine
N,N-diethylaniline
diethylenetriamine
diisopropanolamine
N,N-dimethylethanolamine
N,N-dimethylaniline
2,4-dinitroaniline
diphenylamine
ethyl-para-aminobenzoate
N-ethylethanolamine
N-ethyl-1-naphthylamine
N-ethyl-ortho-toluidine
N-ethylaniline
ethylenediamine
hexamethylenetetraamine
2,4-lutidine
N-methylaniline
methyl anthranilate
p,p'-diaminodiphenyl methane
ortho-nitroaniline
para-nitroaniline
tert-octylamine
piperazine
ethanolamine
isopropanolamine
ortho-toluidine
para-toluidine
2,4-tolyenediamine
triethanolamine
tributylamine
triisopropanolamine
2,4-dimethylxylidine
para-methoxyaniline
nitrilotriacetic acid
N-phenyl-1-naphthylamine Representative but non-exhaustive examples of organic acids which can be alkoxylated according to the present invention are:
formic acid
acetic acid
valeric acid
heptanoic acid
2-ethylhexanoic acid
lauric acid
stearic acid
oleic acid
tall oil acids
hydrogenated tall oil acids
benzoic acid
salicyclic acid
adipic acid
azelaic acid
fumaric acid
citric acid
acrylic acid
aminoacetic acid
para-aminosalicylic acid
anthranilic acid
butyric acid
propionic acid
ricinoleic acid
chloroacetic acid
ortho-chlorobenzoic acid
2,4-dichlorophenoxyacetic acid
tert-decanoic acid
para-aminobenzoic acid
abietic acid
itaconic acid
lactic acid
glycolic acid
malic acid
maleic acid
cinnamic acid
para-hydroxybenzoic acid
methacrylic acid
oxalic acid
myristic acid
palmitic acid
tert-pentanoic acid
phenylacetic acid
mandelic acid
sebacic acid
tallow fatty acids
hydrogenated tallow fatty acids
tartaric acid
trichloroacetic acid
2,4,5-trichlorophenoxyacetic acid
undecylenic acid
crotonic acid
pelargonic acid
acetoacetic acid
para-nitrobenzoic acid
ascorbic acid
nitrilotriacetic acid
naphthenic acids
1-naphthoic acid
trimellitic acid Representative but non-exhaustive examples of various phenols which can be alkoxylated according to the present invention are
phenol ortho-cresol
meta-cresol
para-cresol
2,4-dimethylphenol
2,5-dimethylphenol
2,6-dimethylphenol
ortho-chlorophenol
meta-chlorophenol
para-chlorophenol
para-nitrophenol
para-methoxyphenol
salicylic acid
meta-hydroxyacetophenone
para-aminophenol
ortho-phenylphenol
nonylphenol
octylphenol
t-butyl-para-cresol
hydroquinone
catechol
resorcinol
pyrogallol
1-naphthol
2-naphthol
4,4'-isopropylidenediphenol (bisphenol A)
methyl salicylate
benzyl salicylate
4-chloro-2-nitrophenol
para-t-butylphenol
2,4-di-t-amylphenol
2,4-dinitrophenol
para-hydroxybenzoic acid
8-hydroxyquinoline
methyl para-hydroxybenzoate
2-nitro-para-cresol
ortho-nitrophenol
para-phenylphenol
phenyl salicylate
salicylaldehyde
p-hydroxy benzaldehyde
2-amino-4-chlorophenol
ortho-aminophenol
salicylamide The invention is more concretely described with reference to the examples below wherein all parts and percentages are by weight unless otherwise specified. The examples are provided to illustrate the instant invention and not to limit it.

EXAMPLE 1

A catalyst was prepared in two components. The first component prepared by reacting 10 grams (g) of $BF_3$ with 100 grams of alcohol containing from 12 to 14 carbon atoms (ALFOL 1214, trademark of and sold by Conoco Inc.) The second component was prepared by introducing 60 cubic centimeters (cc) of 0.593M aluminum triethyl in hexane into 100 gram 12 to 14 alcohol. Hexane was subsequently removed by rotary evaporation. Both the first component (0.0175 gram) and in the second component (5.7 gram) were introduced into a stainless steel reactor together with 120 grams of 12 to 14 carbon atom alcohol. After purging with nitrogen at 400 cc per minute for 30 minutes, an alkoxylation was carried out at 170° C. and 40 psig ethylene oxide partial pressure, which was maintained throughout the reaction. Under these conditions, 1.22 moles of ethylene oxide (EO) per mole of alcohol was introduced in 130 minutes. Residual free alcohol in the product was 13.7 weight percent. In contrast, the ethoxylated product produced by $BF_3$ catalyst at the same EO/alcohol mole ratio yielded free alcohol levels of 24%.

EXAMPLE 2

An experiment was carried out exactly as described in Example 1 except that the catalyst was made up of 3.0 grams of the first component and 11.3 grams of the second component. 2.22 moles of EO per mole of alcohol was introduced in 67 minutes. Free alcohol content was 0.60%. A similar experiment carried out using only $BF_3$ catalyst rather than the duel components of the present invention free alcohol content was 8.0%.

EXAMPLE 3

An alcohol with 12 to 14 carbon atoms (ALFOL 1214, 300 g) was ethoxylated as in Example 1, with 2.0 g $SiF_4$ and 10 cc of 0.593M triethylaluminum in hexane as a catalyst mixture. The product after 145 minutes of reaction contained 2.68 mol EO per mol alcohol. The ethylene oxide distribution obtained is compared with that obtained with $BF_3$ catalyst in table 1.

TABLE 1

| Cat. | W % Adduct | | | | | | |
|---|---|---|---|---|---|---|---|
| | 0 | 1 | 2 | 3 | 4 | 5 | 6 |
| $SiF_4$/$(C_2H_5)_3Al$ | 1.2 | 14.0 | 25.7 | 27.6 | 18.5 | 8.7 | 3.2 |
| $BF_3$ | 5.1 | 13.8 | 21.6 | 22.5 | 17.4 | 10.7 | 5.4 |

The data clearly shows $SiF_4$/$(C_2H_5)_3M$ produces an adduct peak much more sharply defined than $BF_3$ alone.

EXAMPLE 4

An experiment was performed as in Example 1 with 2.0 g $BF_3$ etherate and 10 cc of 0.593M triethylaluminum in hexane. The product contained 3.17 mol EO per mol alcohol. The EO distribution of this product was compared with that obtained with $BF_3$ etherate catalyst in table 2.

TABLE 2

| Cat. | W % Adduct | | | | | | |
|---|---|---|---|---|---|---|---|
| | 0 | 1 | 2 | 3 | 4 | 5 | 6 |
| $BF_3$etherate/$(C_2H_5)_3Al$ | 0.3 | 8.4 | 19.6 | 26.5 | 22.3 | 13.3 | 6.4 |
| $BF_3$ etherate | 3.1 | 9.5 | 17.4 | 21.3 | 19.3 | 13.9 | 8.3 |

The data clearly shows that $BF_3$ etherate/$(C_2H_5)_3Al$ produces an adduct peak much more sharply defined than $BF_3$ etherate alone.

EXAMPLE 5

A series of reactions was carried out to determine the effect of metal alkoxide addition to $BF_3$ as an alkoxylation catalyst. Alcohols of various molecular weight were ethoxylated. (ALFOL 1412 molecular weight 205.5; ALFOL 6 molecular weight 1033, a six carbon atom alcohol and ALFOL 610 molecular weight 134.3/, a six to ten carbon atom alcohol, all trademarks of and sold by Conoco Inc.). All reactions were carried out in the same fashion as the following specific reaction.

Gaseous $BF_3$ (10 g) was added to 100 g of six carbon atom alcohol for ease of handling small amount of $BF_3$. Ten grams of this mixture was combined with 3.8 g aluminum alkoxide containing from 2 to 22 carbon atoms in each alkoxide group, and this combination was added to 100 g of a six carbon atom alcohol (ALFOL 6) to form a reaction mixture.

After purging for 30 minutes at 100° C. with $N_2$ (400 cc/min.), the mixture was heated to 170° C., and ethylene oxide was charged to give total pressure of 35 psig. The ethoxylation was performed at this constant pressure for 103 minutes. The product containing 2.67 moles ethylene oxide per mole alcohol. Table 3 shows that the distribution (determined by high pressure liquid chromatography) is very much more peaked than that obtained with $BF_3$ catalyst:

TABLE 3

| Moles EO | Weight %, Adduct | |
|---|---|---|
| | $BF_3$/Alkoxide | $BF_3$ |
| 0 | 0.83 | 3.8 |
| 1 | 10.8 | 12.0 |
| 2 | 26.3 | 20.7 |
| 3 | 29.3 | 22.9 |
| 4 | 19.8 | 18.5 |
| 5 | 9.1 | 11.8 |
| 6 | 3.2 | 6.1 |
| 7 | 0.7 | 2.7 |

Further experiments were repeated using various alcohols. Similar adduct distributions were obtained. The effect of catalyst type on residual unreacted free alcohols is shown in table 4, where $BF_3$ and NaOH catalysts were compared to $BF_3$/alkoxide catalysts.

TABLE 4

CATALYST EFFECT ON RESIDUAL FREE ALCOHOLS

| Alcohol | Mol EO/ Mol ROH | $BF_3$/ Alkoxide | Free Alcohol, Weight % | |
|---|---|---|---|---|
| | | | $BF_3$ | NaOH |
| 1412 | 2.91 | 0.56 | 4.0 | 17.4 |
| 1412 | 2.20 | 2.1 | 8.5 | 24.2 |
| 1412 | 1.31 | 11.4 | 22.2 | 38.5 |
| 1412 | 1.37 | 10.0 | 20.8 | 37.2 |
| 6 | 2.78 | 0.71 | 3.4 | 13.5 |
| 6 | 2.67 | 0.83 | 3.8 | 14.2 |
| 6 | 2.96 | 0.48 | 2.8 | 12.3 |
| 6 | 2.01 | 2.4 | 8.0 | 20.5 |
| 6 | 1.04 | 17.5 | 25.4 | 38.1 |
| 610 | 1.72 | 4.4 | 12.4 | 27.0 |
| 610 | 2.84 | 0.54 | 3.6 | 14.5 |
| 6.0 | 2.08 | 2.3 | 8.3 | 22.0 |

Higher peaking of the distribution of EO in the adducts appears to be directly proportional to the decreased level of unreacted alcohols.

COMPARATIVE EXAMPLE 6

Alkoxylation of an alcohol containing from 12 to 14 carbon atoms was attempted using an aluminum alkoxide catalyst under the conditions of Example 1. No alkoxylation occurred.

While certain embodiments and details have been shown for the purpose of illustrating this invention, it will be apparent to those skilled in this art that various changes and modifications may be made herein without departing from the spirit or scope of the invention.

I claim:

1. Catalysts for alkoxylation reactions comprising at least one material selected from the group consisting of mixtures of $BF_3$ and metal alkoxides, mixtures of $SiF_4$ and metal alkoxides, or mixtures of these, wherein the metal alkoxides have the general formula $M(OR)_n$ wherein each R is, independently, alkyl groups containing from 1 to 20 carbon atoms, M is aluminum or titanium, and n is 3 or 4 depending on the valence of M.

2. A catalyst as described in claim 1 when selected from the group consisting of $BF_3/(C_2H_5O)_3Al$; $BF_3/(CH_3O)_3Al$; $SiF_4/(C_2H_5O)_3Al$; $SiF_4/(CH_3O)_3Al$; $BF_3/(CH_3O)_2(C_2H_5O)Al$; $SiF_4/(CH_3O)_2(C_2H_5O)Al$; $SiF_4/(CH_3O)(C_2H_5O)_2Al$; $BF_3/(CH_3O)_3Al$; $BF_3/(C_2H_5O)_3Al$; $BF_3/(C_{20}H_{41}O)_3Al$; $BF_3/(C_2H_5O)_4Ti$; $BF_3/(CH_3O)_4Ti$; $SiF_4/(C_2H_5O)_4Ti$; $SiF_4/(CH_3O)_4Ti$; $BF_3/(CH_3O)_2(C_2H_5O)_2Ti$; $BF_3/(CH_3O)(C_2H_5O)_3Ti$; $SiF_4/(CH_3O)_2(C_2H_5O)_2Ti$; $BF_3/(CH_3O)_4Ti$; and $BF_3/(C_{20}H_{41}O)_4Ti$.

* * * * *